US012319894B2

(12) United States Patent
Farmer et al.

(10) Patent No.: US 12,319,894 B2
(45) Date of Patent: Jun. 3, 2025

(54) COMPOSITIONS AND METHODS FOR REMOVING SLUDGE FROM OIL STORAGE TANKS

(71) Applicant: Locus Solutions IPCo, LLC, Solon, OH (US)

(72) Inventors: Sean Farmer, Ft. Lauderdale, FL (US); Ken Alibek, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 1260 days.

(21) Appl. No.: 17/048,768

(22) PCT Filed: Apr. 19, 2019

(86) PCT No.: PCT/US2019/028304
§ 371 (c)(1),
(2) Date: Oct. 19, 2020

(87) PCT Pub. No.: WO2019/204715
PCT Pub. Date: Oct. 24, 2019

(65) Prior Publication Data
US 2021/0179974 A1 Jun. 17, 2021

Related U.S. Application Data

(60) Provisional application No. 62/660,069, filed on Apr. 19, 2018.

(51) Int. Cl.
C11D 3/38 (2006.01)
C11D 1/66 (2006.01)
C11D 3/06 (2006.01)
C11D 3/20 (2006.01)
C11D 3/43 (2006.01)
C12N 1/18 (2006.01)

(52) U.S. Cl.
CPC .............. C11D 3/381 (2013.01); C11D 1/667 (2013.01); C11D 3/06 (2013.01); C11D 3/201 (2013.01); C11D 3/43 (2013.01); C12N 1/18 (2013.01); C11D 2111/20 (2024.01)

(58) Field of Classification Search
CPC ....... C11D 3/381; C11D 2111/20; C12N 1/18; C09K 8/582
See application file for complete search history.

(56) References Cited

U.S. PATENT DOCUMENTS

| 3,191,676 | A | 6/1965 | Froning |
| 3,581,824 | A | 6/1971 | Hurd |
| 3,871,956 | A | 3/1975 | Azarowics |
| 4,369,125 | A | 1/1983 | Kragen et al. |
| 4,450,908 | A | 5/1984 | Hitzman |
| 4,487,262 | A | 12/1984 | Venkatesan et al. |
| 4,522,261 | A | 6/1985 | McInerney et al. |
| 4,561,501 | A | 12/1985 | Shaw et al. |
| 4,793,826 | A | 12/1988 | Hayes et al. |
| 4,905,761 | A | 3/1990 | Bryant |
| 5,156,652 | A | 10/1992 | Gregoli et al. |
| 5,165,477 | A | 11/1992 | Shell et al. |
| 5,254,266 | A * | 10/1993 | Barnes ................. E02B 15/046 210/182 |
| 5,284,576 | A | 2/1994 | Weers et al. |
| 5,364,474 | A | 11/1994 | Williford, Jr. |
| 5,869,325 | A | 2/1999 | Crabtree et al. |
| 6,033,901 | A * | 3/2000 | Powell, Jr. ............. B01D 17/00 134/22.18 |
| 6,942,037 | B1 | 9/2005 | Arnold et al. |
| 7,472,747 | B1 | 1/2009 | Brigmon et al. |
| 7,556,654 | B1 | 7/2009 | Nero |
| 7,677,673 | B2 | 3/2010 | Tranquilla et al. |
| 7,681,638 | B2 | 3/2010 | Soni et al. |
| 8,188,012 | B2 | 5/2012 | Weerasooriya et al. |
| 8,316,933 | B2 | 11/2012 | Kohr |
| 9,422,470 | B2 | 8/2016 | Xu et al. |
| 9,441,115 | B2 | 9/2016 | Wu et al. |
| 9,550,937 | B2 | 1/2017 | Campbell et al. |
| 9,683,164 | B2 | 6/2017 | Gunawan et al. |
| 9,725,986 | B2 | 8/2017 | Ku et al. |
| 9,884,986 | B2 | 2/2018 | Gunawan et al. |

(Continued)

FOREIGN PATENT DOCUMENTS

| CN | 1116649 A | 2/1996 |
| CN | 102352227 A | 2/2012 |

(Continued)

OTHER PUBLICATIONS

Amani, H., et al., "Comparative study of biosurfactant producing bacteria in MEOR applications." Journal of Petroleum Science and Engineering, 2010, 75: 209-214.
Amosa, M., et al., "Sulphide Scavengers in Oil and Gas Industry—A Review." NAFTA, 2010, 61(2): 85-92.
Castaneda, L.C., et al., "Current situation of emerging technologies for upgrading of heavy oils." Catalysis Today, 2014, 220-222: 248-273.
Das, N., et al., "Microbial Degradation of Petroleum Hydrocarbon Contaminants: An Overview." Biotechnology Research International, 2010, 2011, Article ID 941810: 1-13.
Daverey, A., et al., "Production of sophorolipids by the yeast *Candida bombicola* using simple and low cost fermentative media." Food Research International, 2009, 42: 499-504.
De Almeida, D.G., et al., "Biosurfactants: Promising Molecules for Petroleum Biotechnology Advances." Frontiers in Microbiology, 2016, 7(1718): 1-14.

(Continued)

Primary Examiner — Jonathan M Hurst
(74) Attorney, Agent, or Firm — SALIWANCHIK, LLOYD & EISENSCHENK

(57) ABSTRACT

The subject invention provides microbe-based products, as well as their use to improve oil production and oil transmission and refining by, for example, remediating the disposable layers in oil tanks and other oil storage units. The subject invention can be used to remediate a sludge layer and/or other dissolved solid layers that form in oil storage tanks. Advantageously, the subject invention can decrease the cost of mechanical remediation of disposable layers, and aid in the recovery of more pure hydrocarbons from crude fluids.

7 Claims, No Drawings

(56) References Cited

U.S. PATENT DOCUMENTS

| | | |
|---|---|---|
| 10,023,787 B2 | 7/2018 | Benoit et al. |
| 10,190,038 B2 | 1/2019 | Armstrong et al. |
| 10,947,444 B2* | 3/2021 | Farmer ............... C09K 8/584 |
| 2001/0056047 A1 | 12/2001 | Meine et al. |
| 2004/0171512 A1 | 9/2004 | Furuta et al. |
| 2004/0231845 A1 | 11/2004 | Cooke, Jr. |
| 2007/0092930 A1 | 4/2007 | Lal et al. |
| 2007/0125536 A1 | 6/2007 | Acock et al. |
| 2007/0151726 A1 | 7/2007 | Crews et al. |
| 2008/0167445 A1 | 7/2008 | Podella et al. |
| 2008/0280789 A1 | 11/2008 | Welton et al. |
| 2008/0302531 A1 | 12/2008 | Berger et al. |
| 2009/0029879 A1 | 1/2009 | Soni et al. |
| 2010/0044031 A1 | 2/2010 | Fallon et al. |
| 2010/0163230 A1 | 7/2010 | Kotlar |
| 2011/0139262 A1 | 6/2011 | Aburto Anell et al. |
| 2011/0237531 A1 | 9/2011 | Yanagisawa et al. |
| 2011/0290482 A1 | 12/2011 | Weerasooriya et al. |
| 2012/0037368 A1 | 2/2012 | Eick et al. |
| 2012/0055685 A1 | 3/2012 | Sanders et al. |
| 2012/0122740 A1 | 5/2012 | Roldan Carrillo et al. |
| 2012/0292022 A1 | 11/2012 | Choban et al. |
| 2013/0020082 A1 | 1/2013 | Lumsden |
| 2013/0062053 A1 | 3/2013 | Kohr et al. |
| 2013/0264060 A1 | 10/2013 | De Wolf et al. |
| 2013/0319656 A1 | 12/2013 | Brownlee |
| 2014/0073541 A1 | 3/2014 | Ravikiran et al. |
| 2014/0273150 A1* | 9/2014 | Angel .................. C12N 9/94 435/186 |
| 2014/0305649 A1 | 10/2014 | Tang et al. |
| 2014/0315765 A1 | 10/2014 | McDaniel |
| 2014/0323757 A1 | 10/2014 | Kim |
| 2014/0332212 A1 | 11/2014 | Ayers et al. |
| 2014/0360727 A1 | 12/2014 | Milam et al. |
| 2015/0037302 A1 | 2/2015 | Bralkowski et al. |
| 2015/0068950 A1 | 3/2015 | See et al. |
| 2015/0259642 A1 | 9/2015 | Sangwai et al. |
| 2015/0300139 A1 | 10/2015 | Armstrong et al. |
| 2016/0002521 A1 | 1/2016 | Dillon et al. |
| 2016/0145487 A1 | 5/2016 | Alam et al. |
| 2016/0160111 A1 | 6/2016 | Smith et al. |
| 2016/0222280 A1 | 8/2016 | Kohr et al. |
| 2016/0244347 A1 | 8/2016 | Angel |
| 2016/0251565 A1 | 9/2016 | Yanagisawa et al. |
| 2016/0333258 A1 | 11/2016 | Drake et al. |
| 2017/0037301 A1 | 2/2017 | Alwattari |
| 2017/0138135 A1 | 5/2017 | Almutairi |
| 2018/0201531 A1 | 7/2018 | Cohen et al. |
| 2018/0282608 A1 | 10/2018 | Gopal et al. |
| 2019/0292436 A1 | 9/2019 | Mason et al. |
| 2019/0359562 A1 | 11/2019 | Lyman et al. |

FOREIGN PATENT DOCUMENTS

| | | |
|---|---|---|
| CN | 102399547 A | 4/2012 |
| CN | 102925397 A | 2/2013 |
| CN | 103409182 A | 11/2013 |
| CN | 103449696 A | 12/2013 |
| CN | 104109646 A | 10/2014 |
| CN | 104711047 A | 6/2015 |
| CN | 104974952 A | 10/2015 |
| CN | 105154050 A | 12/2015 |
| CN | 103614131 B | 1/2016 |
| CN | 105567580 A | 5/2016 |
| CN | 105753283 A | 7/2016 |
| CN | 108373912 A | 8/2018 |
| GB | 2450204 A | 12/2008 |
| JP | 2010200695 A | 9/2010 |
| JP | 2016000017 A | 1/2016 |
| KR | 101481459 B1 | 1/2015 |
| WO | 03031540 A1 | 4/2003 |
| WO | 2007129332 A1 | 11/2007 |
| WO | 2010111226 A2 | 9/2010 |
| WO | 2012010407 A1 | 1/2012 |
| WO | 2013110132 A1 | 1/2013 |
| WO | 2014152350 A1 | 9/2014 |
| WO | 2015093934 A1 | 6/2015 |
| WO | 2015167864 A1 | 11/2015 |
| WO | 2016074904 A1 | 5/2016 |
| WO | 2016196680 A1 | 12/2016 |
| WO | 2017040903 A1 | 3/2017 |
| WO | 2017044953 A1 | 3/2017 |
| WO | 2018049182 A2 | 3/2018 |
| WO | 2018107162 A1 | 6/2018 |
| WO | 2018129299 A1 | 7/2018 |
| WO | 2018148265 A2 | 8/2018 |
| WO | 2018148397 A3 | 8/2018 |
| WO | 2018160995 A1 | 9/2018 |
| WO | 2018191172 A1 | 10/2018 |
| WO | 2018231791 A1 | 12/2018 |
| WO | 2018237137 A1 | 12/2018 |
| WO | 2019022996 A1 | 1/2019 |
| WO | 2019022998 A1 | 1/2019 |
| WO | 2019046183 A1 | 3/2019 |
| WO | 2019067356 A1 | 4/2019 |
| WO | 2019089730 A1 | 5/2019 |
| WO | 2019094615 A1 | 5/2019 |
| WO | 2019133555 A1 | 7/2019 |
| WO | 2019191296 A1 | 10/2019 |
| WO | 2019200054 A1 | 10/2019 |
| WO | 2019222168 A1 | 11/2019 |
| WO | 2020006194 A1 | 1/2020 |

OTHER PUBLICATIONS

De Brito, D., Biosurfactants from renewable raw materials, Universidade do Minho Departamento de Engenharia Biologica, Nov. 2013, pp. 1-93.

De Oliveira, M., et al., "Review: Sophorolipids A promising Biosurfactant and it's Applications." International Journal of Advanced Biotechnology and Research, 2015, 6(2): 161-174.

Elshafie, A.E., et al., "Sophorolipids Production by Candida Bombicola ATCC 22214 and its Potential Application in Microbial Enhanced Oil Recovery." Frontiers in Microbiology, 2015, 6(1324): 1-11.

El-Sheshtawy, H.S., et al., "Production of Biosurfactants by Bacillus Licheniformis and Candida Albicans for Application in Microbial Enhanced Oil Recovery." Egyptian Journal of Petroleum, 2016, 25: 293-298.

Ghojavand, H., et al., "Isolation of Thermotolerant, halotolerant, Facultative Biosurfactant-Producing Bacteria." Applied Microbiology and Biotechnology, 2008, 80: 1073-1085.

Gudina, E.J., et al., "Biosurfactant-producing and oil-degrading Bacillus subtilis strains enhance oil recovery in laboratory sand-pack columns." Journal of Hazardous Materials, 2013, 261: 106-113.

Ines, M., et al., "Glycolipids Biosurfactants; Potential related Biomedical and Biotechnological Applications." Carbohydrate Research, 2015: 1-46.

Kaur, K. et al., "Biosurfactant production by yeasts isolated from hydrocarbon polluted environments." Environmental Monit Assess, 2017, 189(603): 1-13.

Kurtzman, C.P., et al., "Production of sophorolipid biosurfactants by multiple species of the Starmerella (Candida) bombicolayeast clade." FEMS Microbiol Lett, 2010, 311: 140-146.

Liu, X., et al., "Recovery of crude oil from oily sludge in an oilfield by sophorolipid." Petroleum Science and Technology, 2019, 37(13): 1582-1588.

Ma, X., et al., "Surface and biological activity of sophorolipid molecules produces by Wickerhamiella domercqiae var. sophorolipid CGMCC 1576." Journal of Colloid and Interface Science, 2012, 376: 165-172.

Nur, H.A., et al., "Saccharomyces cerevisiae from Baker's Yeast for Lower Oil Viscosity and Beneficial Metabolite to Improve Oil Recovery: An Overview." Applied Mechanics and Materials, 2014, 625: 522-525.

Pacwa-Plociniczak, M., et al., "Environmental Applications of Biosurfactants: Recent Advances." International Journal of Molecular Sciences, 2011, 12: 633-654.

(56) References Cited

OTHER PUBLICATIONS

Rocha E Silva, F.C.P., et al., "Yeasts and bacterial biosurfactants as demulsifiers for petroleum derivative in seawater emulsions." AMB Expr., 2007, 7(202): 1-13.
Santos, D.K.F., et al., "Biosurfactants: Multifunctional Biomolecules of the 21st Century." International Journal of Molecular Sciences, 2016, 17(401): 1-31.
Sen, R., "Biosurfactants: Advances in Experimental Medicine and Biology." Landes Bioscience and Springer Science +Business Media, LLC, 2010, 672: 1-331.
Shah, M.U.H., et al., "Production of sophorolipids by *Starmerella bombicola* yeast using new hydrophobic substrates." Biochemical Engineering Journal, 2017, 127: 60-67.
Silva, R., et al., "Applications of Biosurfactants in the Petroleum Industry and the Remediation of Oil Spills." International Journal of Molecular Sciences, 2014, 15: 12523-12542.
Umar, Z.D., et al., "Rapid biodegradation of polycyclic aromatic hydrocarbons (PAHs) using effective Cronobacter sakazakii MM045 (KT933253)." MethodsX, 2017, 4: 104-117.
Wadekar, S., et al., "Sophorolipid Production by Starmerella bombicola (ATCC 22214) from Virgin and Waste Frying Oils, and the Effects of Activated Earth Treatment of the Waste Oils." J Am Oil Chem Soc, 2012, 89: 1029-1039.
Youssef, N., et al., "In Situ Biosurfactant Production by Bacillus Strains Injected into a Limestone Petroleum Reservoir." Applied and Environmental Microbiology, Feb. 2007, 73(4): 1239-1247.
Zafra, G., et al., "Biodegradation of polycyclic aromatic hydrocarbons by *Trichoderma* species: a mini review." Environ Sci Pollut Res, 2015, 22: 19426-19433.

\* cited by examiner

COMPOSITIONS AND METHODS FOR REMOVING SLUDGE FROM OIL STORAGE TANKS

CROSS-REFERENCE TO RELATED APPLICATION

This application is a National Stage Application of International Application No. PCT/US2019/028304, filed Apr. 19. 2019; which claims priority to U.S. Provisional Patent Application No. 62/660,069, filed Apr. 19, 2018, both of which are incorporated herein by reference in their entirety.

BACKGROUND OF THE INVENTION

Crude oil, once extracted from an oil-bearing formation, is often stored and/or transported in large tanks, which can have a diameter ranging from 100 to 400 feet, or more, and can hold volumes ranging from 500 gallons to 1 million or more barrels of crude oil. When oil is stored in these tanks a buildup of sediment can occur, decreasing the usable capacity of the tank and plugging oil discharge lines when oil is pumped out of the tank. Thus, periodic cleaning of oil storage tanks is crucial for removing these sediments, ensuring the integrity of the tank structure and maintaining the capacity of the tank.

The combination of sediments that build up over time, often referred to as "sludge," comprises a mixture of deposits that varies from tank to tank, and depends upon the composition of the oil or oils that have been stored in a particular tank. The types of formation from which stored oil was extracted, as well as the extent to which the oil was processed and/or refined, also contribute to the make-up of the sludge in a tank.

In general, sludge can form from, for example, higher molecular weight hydrocarbons, entrained water, rust and scales from piping and tank walls, inorganic debris, sand, scale, fracking polymers, and process solids. These components separate from the volume of liquid hydrocarbons in the storage tank over time due to gravity, thus forming a sediment layer, which becomes sludge.

More specifically, sludge can comprise different combinations of inorganic and organic materials that include, but are not limited to, organic resins, asphaltenes, paraffin compounds, heavy hydrocarbons, light hydrocarbons, gels, emulsions, rust particles, rust scales, mineral sediments, refining or petrochemical process solids, catalyst fines, pyrophoric iron sulfide deposits, soft lines, coating particles, coating scales, rags, rocks, sand and gravel.

Over time, the heavier elements in the stored oil will continue to migrate to the bottom of the tank and enter the sludge. As these heavier components concentrate, the sludge becomes more viscous and may even solidify. Because a large storage tank can hold thousands of barrels or more, and large volumes of oil pass in and out of the storage tank between cleanings, the tank can accumulate sludge from an enormous volume of oil.

Sludge removal or tank cleaning is required when sludge buildup interferes with or reduces the efficiency of the storage tank operation. Conventional techniques can be classified as sludge fluidization or sludge excavation. With sludge fluidization, large quantities of heated or ambient temperature diluents or cutter stock (various types of light oils such as diesel oil, light cycle oil, or light crude oil) are circulated through the tank and mixed into the sludge to reduce its viscosity, modify surface tension and disperse the sludge. The fluids can then be pumped out of the tank using, for example, a centrifugal pump.

After circulation, a substantial amount of organic solids (resins, asphaltenes), inorganic solids (rust scale, surface coatings, mineral sediments) and debris will typically remain in the tank. Cutter stock can be injected and circulated to disperse some or this residual sludge, but it cannot be removed easily by the cutter stock method alone. Sometimes, the residual sludge must be manually pushed to sludge pumps positioned inside the tank and/or at a sump. Residual sludge that contains rust scale or other large debris must be manually removed by shovels or by air vacuum trucks. Additional removal can be achieved using diesel or other light cycle oil with manual scrubbing, which can remove sticky sludge attached to floors and walls of the tank. Scrapers may be required, however, for particularly stubborn sludge and residue.

De-oiling of the interior surfaces of the tank can be performed with a soap injection pump and manual scrubbing, followed by a wash with a high pressure hose. Workers enter the inside of the tank through a removable, manway door in the side of the tank. At this time, high pressure water is introduced into the sediment using a water jet pipe or a water cannon, creating a water and sediment slurry. The slurry is then vacuumed into a vacuum truck tank and carried to a disposal site. The wash water can then be pumped out for disposal. The floor may be detailed by squeegee and rags, as required, to remove visible oil and oily stains from tank surfaces.

In addition to sludge fluidization, sludge excavation can be used for sludge removal and cleaning. This method consists of manual or mechanical methods to physically excavate, collect, and remove the sludge from a tank in its existing condition. This method is time consuming, labor intensive and expensive. Furthermore, the personnel working within the tank are exposed to potential health risks, as well as possible injury.

Both sludge fluidization and excavation have significant drawbacks. Sludge fluidization methods can be inefficient and time consuming, taking up to, for example, 3 months to clean a 300 foot diameter tank. Additionally, when the temperature decreases, re-solidification of sludge can result. Furthermore, addition of cutter stock fluid can impact the physical and chemical characteristics of recovered oil, and because such a high volume of cutter stock is required, the processing or re-refining of cutter stock to remove dispersed sludge is also extensive.

Lastly, fluidization methods can pose safety concerns due to increased flammability and the emission of organic compounds, which can be harmful for manual laborers to inhale when they are inside or around the tanks. For example, during the formation of the water and sediment slurry during de-oiling, dangerous gases can be released that can cause illness or death without a gas mask.

Excavation can also be inefficient and time consuming, even more so than fluidization. Additionally, the safety concerns for workers are even greater due to the extended periods of time spent working in a confined space. Furthermore, excavation results in high volumes of waste that must be disposed of properly. Despite these drawbacks, manual removal is often the only removal mechanism available for some types of tank bottom sludge conditions. Even when fluidization is employed, the sludge might not be sufficiently fluid to be pumped out of the tank, and at least some portion must be manually removed.

For recovery of oil from sludge once it has been pumped from a tank, methods often employ the use of large-scale centrifuges to separate solids from liquids. This process can take days, or even months, to extract the solids from the oil because of the high volume of solids remaining in the oil, and the corresponding heaviness of the oil.

Efficient production of oil depends upon the proper functioning of equipment and the ability of processing operations to extract the maximum amount of usable hydrocarbons from crude oil fluids. Thus, there is a continuing need for simple, cost-effective and safe methods of removing sludge from oil storage tanks and vessels.

BRIEF SUMMARY OF THE INVENTION

In one embodiment, the subject invention provides microbe-based products, as well as their use, to improve oil production by, for example, enhancing methods for removing sludge from oil storage tanks. The subject invention utilizes biochemical-producing microbes and/or their growth by-products, including, for example, biosurfactants, solvents, enzymes, or other useful metabolites. Advantageously, the microbe-based products and methods of the subject invention are non-toxic, environmentally-friendly, operational-friendly and cost-effective.

The compositions and methods of the subject invention can separate out solids and impurities entrained in crude oil fluids and deposits present in oil storage containers. For example, the subject invention can be used to dissolve sludge, and to destabilize and separate out sands, scales, clay, dissolved solids, asphaltenes and/or paraffins from sludge and crude fluids. Advantageously, in certain embodiments, this can be achieved in only a few hours, for example 1 to 24 hours. Oil can then be recovered from the tank and processed more quickly in, for example, refineries, thus increasing crude production yields and efficiency.

In preferred embodiments, sludge cleaning compositions are provided, the compositions comprising one or more microorganisms, one or more biosurfactants, one or more solvents and an ammonium salt. Optionally, the composition can also comprise nutrients for microbial growth, including, for example, sources of carbon, nitrogen, potassium, magnesium, phosphorous, micronutrients and proteins.

In certain embodiments, the one or more microorganisms are yeasts. In preferred embodiments, the yeasts are live at the time of use.

In specific embodiments, the yeasts are baker's and/or brewer's yeast (*Saccharomyces cerevisiae*). The baker's and/or brewer's yeasts can be used on its own or in conjunction with a yeast fermentation product comprising water and a culture of a second yeast, e.g., *Wickerhamomyces anomalus*. In certain embodiments, the ratio of water to *W. anomalus* culture in the yeast fermentation product is about 10:1 to 2:1.

When a combination of baker's and/or brewer's yeast and the *W. anomalus* fermentation product is used, the ratio of *S. cerevisiae* to *W. anomalus* product is preferably about 10:1 to 2:1.

In specific embodiments, the total yeast content of the sludge removal composition is about 5 g/L to about 30 g/L.

In one embodiment, the composition further comprises one or more biosurfactants. Biosurfactants useful according to the subject invention include, for example, low-molecular-weight glycolipids, lipopeptides, fatty acid esters, fatty acid ethers, flavolipids, phospholipids, and high-molecular-weight polymers/biopolymers such as lipoproteins, lipopolysaccharide-protein complexes, and/or polysaccharide-protein-fatty acid complexes. Preferably, the biosurfactants are produced by microorganisms.

In one embodiment, the biosurfactants can comprise one or more glycolipids such as, for example, rhamnolipids (RLP), rhamnose-d-phospholipids, trehalose lipids, trehalose dimycolates, trehalose monomycolates, mannosylerythritol lipids (MEL), cellobiose lipids, ustilagic acids and/or sophorolipids (SLP) (including lactonic forms and/or acidic forms). In one embodiment, the biosurfactants can comprise one or more lipopeptides, such as, for example, surfactin, iturin, fengycin, arthrofactin, viscosin, amphisin, syringomycin, and/or lichenysin. In one embodiment, the biosurfactants can comprise one or more fatty acid esters and/or one or more fatty acid ethers. In one embodiment, the biosurfactants can comprise one or more other types of biosurfactants, such as, for example, cardiolipin, emulsan, lipomanan, alasan, and/or liposan.

In one embodiment, the biosurfactants can comprise one or more microbial compounds having physical properties and/or behaviors similar to those of biosurfactants, but which are not commonly known as biosurfactants. These compounds can be fatty acid esters and/or fatty acid ethers. In certain embodiments, the fatty acid compounds can comprise carbon chains with 6 to 22 carbon atoms. In certain embodiments, the fatty acid(s) of the fatty acid compounds is unsaturated.

In certain embodiments, the total biosurfactant concentration is about 0.1 g/L to about 20 g/L. In preferred embodiments, the surfactant concentration is no lower than critical micelle concentration (CMC). Such concentration can be calculated by the skilled artisan having the benefit of the subject disclosure.

The biosurfactants can be added in a purified form or in crude form. In one embodiment, the yeast fermentation product comprises additional biosurfactants because the microorganism produces biosurfactants as a growth by-product. In certain embodiments, the biosurfactants work synergistically with solvents and other metabolites that are in the composition and/or that are produced by the microbes.

In certain embodiments, the compositions of the subject invention have advantages over, for example, biosurfactants alone, including one or more of the following: high concentrations of mannoprotein as a part of a yeast cell wall's outer surface; the presence of beta-glucan in yeast cell walls; the presence of biosurfactants in the culture; and the presence of solvents and other metabolites (e.g., lactic acid, ethanol, ethyl acetate, etc.) in the culture.

In certain embodiments, the composition comprises one or more solvents. In one embodiment, the solvent is an alcohol. Preferably, the alcohol is isopropyl alcohol. In specific embodiments, the concentration of isopropyl alcohol is about 5 to about 100 ml/L.

In certain embodiments, the composition further comprises an ammonium salt, for example, monoammonium phosphate (or ammonium dihydrogen phosphate). In specific embodiments, the concentration of monoammonium phosphate is about 1 to about 10 g/L.

In preferred embodiments, the subject invention provides a method for improving oil production efficiency by applying to a storage container having sludge therein, a composition comprising one or more microorganisms, one or more biosurfactants, one or more solvents and an ammonium salt.

The composition can be prepared and mixed prior to being applied to the storage container, or the individual components of the composition can be added separately to the storage container and mixed therein. In preferred embodiments, the storage container is an oil storage tank.

In one embodiment, the composition is a sludge cleaning composition of the subject invention. Optionally, the method can further comprise adding nutrients that are beneficial to microbial growth, such as, for example, nitrogen, potassium, phosphorus, magnesium and/or carbon.

In one embodiment, the sludge cleaning composition is mixed within a storage container for a period of time sufficient to dissolve the sludge and form an emulsion comprising the composition and oil, water and sludge components. Mixing can be performed using any mixing device or technique, for example, a pump to inject fluids (e.g., gas (air) and/or liquid) under pressure to continuously agitate the liquids within the tank. In one embodiment, the storage container has a built-in mixing system, such as, for example, a mechanical stirring apparatus.

Preferably, the mixing takes place continuously for a duration of about 1 to 6 hours or more, or at least 1, 2, 3, 4, 5 or 6 hours. Then, the emulsion can be allowed to sit for 2 to 3 hours, up to 12 to 24 hours, or more, or until three separate layers form out of the emulsion, said layers comprising: a top oil layer, a middle water and/or brine layer, and a bottom solid or semi-solid layer of sediment comprising, for example, sand, scale, clay, paraffins, asphaltenes and/or other solid sludge particles.

The amount of the sludge cleaning composition added to the container is determined based on a ratio of units of composition to sludge. In certain embodiments, the ratio of composition to sludge is about 10:1 to 2:1. In specific embodiments, the composition to sludge ratio is about 2:1.

In one embodiment, the storage container is a large storage tank, for example, having a diameter of 300 to 400 feet. In certain embodiments, a portion of sludge can be removed from the large storage tank via robotic or manual methods and placed into a smaller storage tank, for example, a tank ⅓ or ½ the size of the large storage tank. Then, the methods according to the subject invention can be carried out in the smaller storage tank, which can reduce the time required for sludge remediation.

In one embodiment, the method further comprises, after the layers have separated within the tank, removing the top oil layer from the storage tank and placing the oil layer into a centrifuge. Advantageously, in one embodiment, the oil layer has less sand and scale remaining in it than it would have if it were not treated with the subject composition. Thus, the centrifuge can operate at a faster speed, thereby reducing the amount of time required for the centrifuge process to separate the layers. Accordingly, residual oil can be separated in a matter of hours or days to be sent to oil refineries. Furthermore, the residual oil that is recovered from the centrifuge can be processed and/or refined more efficiently than untreated residual oil.

In one embodiment, after the oil layer is removed from the storage tank, the water and/or brine phase layer can be removed, for example, by pumping. The water and/or brine can be sent to a water treatment facility, and/or it can be recycled, for example, as frac fluid in fracking wells.

After the oil and water layers have been removed from the storage tank, the solid sludge sediment layer is left behind. In one embodiment, the storage tank and sludge therein can be treated again with the sludge cleaning composition. For example, the sludge cleaning composition can be applied to the tank, mixed, and then allowed to sit and dissolve and/or separate the remaining sludge.

In one embodiment, the remaining sludge layer can be manually or mechanically removed from the tank, using robotics, mechanized excavation techniques, or using shovels and manpower. Whether to apply the sludge cleaning composition or to manually remove the remaining sludge can depend upon, for example, the thickness of the remaining layer, the composition and/or age of the sludge, the size of the tank, and other factors.

The subject compositions and methods can be administered in sludge-containing tanks utilized during production, transportation, storage, and/or refining of crude oil. For example, the subject products can be applied to a storage tank at or near the site of recovery, a tanker used for transporting the oil, and/or a tank where crude oil is deposited and held prior to refining.

Advantageously, in some embodiments, the present invention can be used without releasing large quantities of inorganic compounds into the environment. Additionally, in preferred embodiments, the compositions and methods can utilize components that are biodegradable and toxicologically safe. Thus, the present invention can be used in all possible operations of oil and gas production as an environmentally-friendly treatment.

DETAILED DESCRIPTION

In one embodiment, the subject invention provides microbe-based products, as well as their use, to improve oil production by, for example, enhancing methods for removing sludge from oil storage tanks. The subject invention utilizes biochemical-producing microbes and/or their growth by-products, including, for example, biosurfactants, solvents, enzymes, or other useful metabolites. Advantageously, the microbe-based products and methods of the subject invention are non-toxic, environmentally-friendly, operational-friendly and cost-effective.

The compositions and methods of the subject invention can separate out solids and impurities entrained in crude oil fluids and deposits present in oil storage containers. For example, the subject invention can be used to dissolve sludge, and to destabilize and separate out sands, scales, clay, dissolved solids, asphaltenes and/or paraffins from sludge and crude fluids. Advantageously, in certain embodiments, this can be achieved in only a few hours, for example 1 to 24 hours. Oil can then be recovered from the tank and processed more quickly in, for example, refineries, thus increasing crude production yields and efficiency.

In preferred embodiments, sludge cleaning compositions are provided, the compositions comprising one or more microorganisms, one or more biosurfactants, one or more solvents and an ammonium salt. Methods are also provided for cleaning sludge from a storage container having sludge therein, wherein a composition of the subject invention is applied to the container.

The composition can be prepared and mixed prior to being applied to the storage container, or the individual components of the composition can be added separately to the storage container and mixed therein. In preferred embodiments, the storage container is an oil storage tank.

Selected Definitions

As used herein, reference to a "microbe-based composition" means a composition that comprises components that were produced as the result of the growth of microorganisms or other cell cultures. Thus, the microbe-based composition may comprise the microbes themselves and/or products of microbial growth. The microbes may be in a vegetative state, in spore form, in mycelial form, in any other form of propagule, or a mixture of these. The microbes may be planktonic or in a biofilm form, or a mixture of both. The products of growth may be, for example, metabolites, cell membrane components, expressed proteins, and/or other cellular components. The microbes may be intact or lysed; active or inactive. In some embodiments, the microbes are present, with medium in which they were grown, in the microbe-based composition. The microbes may be removed from the composition, or they may be present at, for example, a concentration of $1\times10^4$, $1\times10^5$, $1\times10^6$, $1\times10^7$, $1\times10^8$, $1\times10^9$, $1\times10^{10}$, $1\times10^{11}$, $1\times10^{12}$, or $1\times10^{13}$ or more propagules per milliliter of the composition. As used herein, a propagule is any portion of a microorganism from which a new and/or mature organism can develop, including but not limited to, cells, spores (e.g., reproductive spores, endospore and exospores), mycelia, cysts, conidia, buds and seeds.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added, or it may have ingredients removed therefrom. Additional ingredients can include, for example, stabilizers, buffers, appropriate carriers, such as water, salt solutions, or any other appropriate carrier, added nutrients to support further microbial growth, non-nutrient growth enhancers, and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, an "isolated" or "purified" nucleic acid molecule, polynucleotide, polypeptide, protein or organic compound, such as a small molecule, is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of other molecules, or the amino acids that flank it, in its naturally-occurring state.

As used herein, reference to an "isolated" microbial strain means that the strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

A "metabolite" refers to any substance produced by metabolism (e.g., a growth by-product) or a substance necessary for taking part in a particular metabolic process. Examples of metabolites can include, but are not limited to, enzymes, acids, solvents, gases, alcohols, proteins, carbohydrates, vitamins, minerals, microelements, amino acids, polymers, and surfactants.

As used herein, "reduces" means a negative alteration of at least 1%, 5%, 10%, 25%, 50%, 75%, or 100%.

As used herein, "surfactant" means a compound that lowers the surface tension (or interfacial tension) between two liquids or between a liquid and a solid. Surfactants act as, e.g., detergents, wetting agents, emulsifiers, foaming agents, and/or dispersants. A "biosurfactant" is a surface-active substance produced by a living cell.

As used herein, "heavy oil" or "heavy hydrocarbons" mean viscous hydrocarbon substances. Heavy hydrocarbons may comprise highly viscous hydrocarbons such as heavy oil, extra heavy oil, bitumen, tar, petcoke, asphaltenes and/or asphalt. Heavy oils and extra heavy oils are highly viscous with a density close to or even exceeding water. The phrase "heavy oil" as used herein also includes "extra heavy oil." Heavy hydrocarbons may comprise moderate to high quantities of paraffins, resins and asphaltenes, as well as smaller concentrations of sulfur, oxygen, and nitrogen. Heavy hydrocarbons may also include aromatics or other complex ring hydrocarbons. Additional elements, e.g., metals, may also be present in heavy hydrocarbons in trace amounts.

Heavy hydrocarbons may be classified by API gravity. Heavy hydrocarbons generally have an API gravity below about 20° or lower. Heavy oil, for example, generally has an API gravity of about 10-20°, whereas extra heavy oil generally has an API gravity below about 12°. The viscosity of heavy hydrocarbons is generally greater than about 200 cp at reservoir conditions, and that of extra heavy oil is generally about 10,000 cp or more. (For reference, as used herein, "light oil" or "light hydrocarbons" have an API gravity above 20°, preferably above about 25°, even more preferably above 30° to 31°, and a viscosity of about 1 to 100 cp).

As used herein, "impurity" or "contaminant" refers to any substance that causes another substance or object to become fouled, contaminated or impure. Impurities can be living or non-living and can be inorganic or organic substances or deposits. Furthermore, impurities can include, but are not limited to, hydrocarbons, such as petroleum, tar sands or asphaltenes; fats, oils and greases (FOG), such as cooking grease and lard; lipids; waxes, such as paraffin; resins; biofilms; or any other substances referred to as, for example, dirt, dust, scale (including calcium carbonate, calcium chloride, barium carbonate, barium chloride, and iron sulfide), sludge, crud, slag, grime, scum, plaque, buildup, or residue. Sludge and its individual components can be included in the phrase "impurity."

As used herein, "sludge" or "sludge layer" refers to a phase in crude fluids, usually present at the bottom of oil storage tanks, comprising heavy hydrocarbons, such as paraffins and asphaltenes, and other impurities such as sand, scale, clay, rust and heavy metals. The composition of a sludge layer can vary greatly between different oil tanks.

As used herein, "cleaning" as used in the context of sludge removal, means removal or reduction of sludge and its components. Cleaning can include remediating, separating, purifying, Befouling, decontaminating, dissolving, clearing, treating and/or unclogging. Cleaning can further include controlling, inhibiting or preventing further formation of sludge.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic arid novel characteristic(s)" of the claimed invention. Use of the term "comprising" contemplates other embodiments that "consist" or "consist essentially of" the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

All references cited herein are hereby incorporated by reference in their entirety.

Sludge Cleaning Compositions

In preferred embodiments, sludge cleaning compositions are provided, the compositions comprising one or more microorganisms, one or more biosurfactants, one or more solvents and an ammonium salt. Optionally, the composition can also comprise nutrients for microbial growth, including, for example, sources of carbon, nitrogen, potassium, magnesium, phosphorous, micronutrients and proteins.

The compositions and methods of the subject invention can separate out solids and impurities entrained in crude oil fluids and deposits present in oil storage containers. For example, the subject invention can be used to dissolve sludge, and to destabilize and separate out sands, scales, clay, dissolved solids, asphaltenes and/or paraffins from sludge and crude fluids. Advantageously, in certain embodiments, this can be achieved in only a few hours, for example 1 to 24 hours. Oil can then be recovered from the tank and processed more quickly in refineries, thus increasing crude production yields and efficiency.

The microorganisms useful according to the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganism is any yeast or fungus, including, for example, *Acaulospora, Aspergillus, Aureobasidium* (e.g., *A. pullulans*), *Blakeslea, Candida* (e.g., *C. albicans, C. apicola*), *Debaryomyces* (e.g., *D. hansenii*), *Entomophthora, Fusarium, Hanseniaspora* (e.g., *H. uvarum*), *Hansenula, Issatchenkia, Kluyveromyces, Mortierella, Mucor* (e.g., *M. piriformis*), *Penicillium, Phythium, Phycomyces, Pichia* (e.g., *P. anomala, P. guielliermondii, P. occidentalis, P. kudriavzevii*), *Pseudozyma* (e.g., *P. aphidis*), *Rhizopus, Saccharomyces* (*S. cerevisiae, S. boulardii sequela, S. torula*), *Starmerella* (e.g., *S. bombicola*), *Torulopsis, Thraustochytrium, Trichoderma* (e.g., *T. reesei, T. harzianum, T. virens*), *Ustilago* (e.g., *U. maydis*), *Wickerhamomyces* (e.g., *W. anomalus*), *Williopsis*, and/or *Zygosaccharomyces* (e.g., *Z. bailii*).

In certain embodiments, the yeasts are live at the time of use. In specific embodiments, the yeasts are baker's and/or brewer's yeast (*Saccharomyces cerevisiae*). In some embodiments, the baker's and/or brewer's yeast can be in the form of "active dry yeast," which comprises granules made up of live yeast cells encapsulated in dry, dead yeast cells and some growth medium. It is commonly used for baking breads and brewing alcoholic beverages.

In some embodiments, the term active dry yeast can include yeast products labeled as "instant yeast" and/or "rapid-rise yeast," which comprise smaller-sized granules and, in some instances, a greater concentration of live cells per granule. In some embodiments, the active dry baker's and/or brewer's yeast can comprise traces of ascorbic acid.

In some embodiments, when active dry yeast is used, it is first dissolved in water prior to being added to the composition. In other embodiments, the active dry yeast is added to the composition in dry form.

The baker's and/or brewer's yeasts can be used in the composition on its own or in conjunction with a yeast fermentation product comprising a second yeast.

In preferred embodiments, the yeast fermentation product comprises water and a culture of a *Pichia* spp. yeast or a relative thereof, e.g., *Wickerhamomyces anomalus* (*Pichia anomala*) or *Meyerozyma guilliermondii* (*Pichia guilliermondii*). In specific embodiments, the yeast is *Wickerhamomyces anomalus*. *W. anomalus* is an effective producer of biosurfactants (e.g. glycolipids and/or phospholipids), ethyl acetate, and other metabolites useful for sludge removal, such as solvents and enzymes.

The yeast fermentation product can comprise the fermentation broth containing the second yeast and/or the metabolites produced by the second yeast and/or any residual nutrients. The yeasts in the yeast fermentation product may be in an active or inactive form. In certain embodiments, the yeasts are active at the time the composition is used.

In one embodiment, the yeast fermentation product can be obtained via cultivation of a yeast, such as, for example, *W. anomalus*, using processes ranging from small to large scale. The cultivation process can be, for example, submerged cultivation, solid state fermentation (SSF), and/or modified/combined forms thereof.

In one embodiment, the yeast fermentation product is produced on a substrate with ample surface area onto which the yeasts can attach and propagate, such as, for example, corn flour, rice, soybeans, chickpeas, pasta, oatmeal or beans. The entire fermentation medium with yeast cells growing throughout, and any growth by-products thereof (e.g., enzymes, solvents, and/or biosurfactants) can be harvested after, for example, 3-5 days of cultivation at 25-30°

C. The culture can be washed out and used in liquid form, or blended with the solid substrate, milled and/or micronized, and optionally, dried.

In an alternative embodiment, the yeast fermentation product is obtained using submerged fermentation, wherein the fermentation broth after 7 days of cultivation at 25-30° C. can contain the yeast cell suspension and, for example, 4 g/L or more of biosurfactants.

The yeast fermentation product may be used directly without extraction, purification and/or storage. If desired, extraction and purification can be easily achieved using standard extraction and/or purification methods or techniques described in the literature. Advantageously, direct usage of the yeast-based product preserves a high viability of the microorganisms, reduces the possibility of contamination from foreign agents and undesirable microorganisms, and maintains the activity of the by-products of microbial growth.

In some embodiments, the yeast fermentation product is mixed with oil, water and/or brine fluids and, if desired, diluted by 5 to 1,000 times. In certain embodiments, the ratio of water to *W. anomalus* culture in the yeast fermentation product is about 10:1 to 2:1, about 9:1 to 3:1, about 8:1 to 4:1, about 7:1 to 5:1, or about 6:1.

In some embodiments, if desired, the yeasts and/or broth resulting from their growth can be removed from the vessel in which they are grown and mixed directly into the sludge cleaning composition or transferred to an oil storage tank for immediate use.

In certain embodiments, the compositions of the subject invention have advantages over, for example, purified microbial metabolites and/or synthetic chemical treatments, due to the use of yeasts. These advantages include one or more of the following: high concentrations of mannoprotein as a part of a yeast cell wall's outer surface; the presence of beta-glucan in yeast cell walls; the presence of biosurfactants in the culture; and the presence of solvents and other metabolites (e.g., lactic acid, ethanol, ethyl acetate, etc.) in the culture.

In specific embodiments, the total yeast content of the sludge removal composition is about 5 g/L to about 30 g/L, about 10 g/L to about 25 g/L, or about 20 g/L.

When a combination of baker's and/or brewer's yeast and the *W. anomalus* fermentation product is used, the ratio of *S. cerevisiae* to *W. anomalus* product is preferably about 10:1 to 2:1, about 9:1 to 3:1, about 8:1 to 4:1, about 7:1 to 5:1, or about 6:1.

In one embodiment, the composition further comprises one or more biosurfactants. Biosurfactants are a structurally diverse group of surface-active substances produced by microorganisms. Biosurfactants are biodegradable and can produced using selected organisms in or on renewable substrates.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces. Furthermore, biosurfactants accumulate at interfaces, and reduce the surface and interfacial tension between the molecules of liquids, solids, and gases, thus leading to the formation of aggregated micellar structures in solution.

Biosurfactants according to the subject invention include, for example, low-molecular-weight glycolipids, lipopeptides, fatty acid ester compounds, fatty acid ether compounds, flavolipids, phospholipids, and high-molecular-weight polymers/biopolymers such as lipoproteins, lipopolysaccharide-protein complexes, and/or polysaccharide-protein-fatty acid complexes.

In one embodiment, the biosurfactants can comprise one or more glycolipids such as, for example, rhamnolipids (RLP), rhamnose-d-phospholipids, trehalose lipids, trehalose dimycolates, trehalose monomycolates, mannosylerythritol lipids (MEL), cellobiose lipids, ustilagic acids and/or sophorolipids (SLP) (including lactonic forms and/or acidic forms).

In one embodiment, the biosurfactants can comprise one or more lipopeptides, such as, for example, surfactin, iturin, fengycin, arthrofactin, viscosin, amphisin, syringomycin, and/or lichenysin.

In one embodiment, the biosurfactants can comprise one or more other types of biosurfactants, such as, for example, cardiolipin, emulsan, lipomanan, alasan, and/or liposan.

In one embodiment, the biosurfactants can comprise one or more microbial compounds having physical properties and/or behaviors similar to those of biosurfactants, but which are not commonly known as biosurfactants. These compounds can be fatty acid esters and/or fatty acid ethers. In certain embodiments, the fatty acid compounds can comprise carbon chains with 6 to 22 carbon atoms. In certain embodiments, the fatty acid(s) of the fatty acid compounds is unsaturated.

In one embodiment, the fatty acid ester compounds are oleic fatty acid ethyl esters and/or oleic fatty acid methyl esters (FAME).

In one exemplary embodiment, the composition comprises a sophorolipid at a concentration of about 0.1 g/L to about 20 g/L, about 0.5 g/L to about 10 g/L, or about 2 g/L to about 5 g/L.

In certain embodiments, the total biosurfactant concentration is about 0.1 g/L to about 20 g/L. In preferred embodiments, the surfactant concentration is no lower than critical micelle concentration (CMC). Such concentration can be calculated by the skilled artisan having the benefit of the subject disclosure.

The biosurfactants can be added in a purified form or in crude form. In one embodiment, the yeast fermentation product comprises additional biosurfactants because the microorganism produces biosurfactants as a growth by-product.

In certain embodiments, the biosurfactants work synergistically with solvents and other metabolites that are in the composition and/or that are produced by the microbes.

In certain embodiments, the composition comprises one or more solvents. Examples of solvent(s) that can be utilized according to the subject invention include, but are not limited to, terpenes, terpenoids, alcohols, ionic or semi-ionic liquids, acetates, aliphatic and/or aromatic hydrocarbons, olefins, esters, oxygenates, ketones, acetic acid, kerosene, gasoline, diesel, benzene, ethyl benzenes, propyl benzenes, butyl benzenes, toluene, ethyl toluenes, xylene, pentane, alkylene amines, dioxane, carbon disulfide, mesitylene, cumene, cymenes, saturated aliphatic and/or alicyclic hydrocarbons, naphtha, naphthenes, cyclohexane, decalin, tetralin, heptane, octane, cyclooctane, isooctane, cycloheptane, turpentine, carbon tetrachloride, ether alcohol, pinene, dialkyl ether and/or any combination thereof.

In one embodiment, the solvent is an alcohol, such as, for example, ethanol, methanol, propanol, isopropyl alcohol and/or hexanol. Preferably, the alcohol is isopropyl alcohol. In specific embodiments, the concentration of isopropyl alcohol is about 5 to about 100 ml/L, about 10 to about 50 ml/L, or about 50 ml/L to about 100 ml/L.

In certain embodiments, the composition further comprises an ammonium salt, for example, ammonium hydroxide, ammonium phosphate, monoammonium phosphate, diammonium phosphate, ammonium chloride, or another dibasic or monobasic salt can be included at a concentration of about 1 g/L to about 20 g/L, about 2 g/L to about 10 g/L, or about 3 g/L to about 5 g/L. In a specific embodiment, the salt is monoammonium phosphate.

In some embodiments, additional components can be added to increase the effectiveness of the microbe-based composition and its use in sludge cleaning. For example, in one embodiment, the composition can comprise added purified biosurfactants, and/or non-biological surfactants and/or solvents on top of those already present in the composition.

In one embodiment, ionic or semi-ionic liquids can be added to the composition to increase its effectiveness. Exemplary ionic or semi-ionic liquids suitable for the subject composition include, but are not limited to, ethyl ammonium nitrate, and/or a semi-ionic mixture of glycerin/glycerol with magnesium sulfate heptahydrate ($MgSO_4 \cdot 7H_2O$). In one embodiment, the mixture of glycerol and Epsom salt ($MgSO_4 \cdot 7H_2O$) has a ratio of glycerol to Epsom salt of 1:1 to 1:10, or from 1:1 to 10:1.

In some embodiments, the ionic or semi-ionic liquid can act as a co-solvent and can prevent the formation of ring bonds in hydrocarbon compositions, which is one cause of hydrocarbon precipitation. In one embodiment, the ionic or semi-ionic liquid is present in the composition at a concentration of about 10 ml/L to 200 ml/L, about 20 ml/L to 175 ml/L, about 30 ml/L to 150 ml/l, about 40 ml/L to 125 ml/L, or about 50 ml/L to 100 ml/L.

Other suitable additives, which may be contained in the formulations according to the invention, include substances that are customarily used for such preparations. Example of such additives include surfactants, emulsifying agents, lubricants, buffering agents, solubility controlling agents, pH adjusting agents, preservatives, stabilizers and ultra-violet light resistant agents.

In one embodiment, the composition may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture of these.

In one embodiment, additional components such as an aqueous preparation of a salt, such as sodium bicarbonate or carbonate, sodium sulfate, sodium phosphate, sodium biphosphate, can be included in the formulation.

Other suitable additives can include, for example, terpene alcohols, C8-C14 alcohol ester blends, glycols, glycol ethers, acid esters, diacid esters, petroleum hydrocarbons, amino acids, alkanolamines, and amines, preferably, methyl or isobutyl esters of C4-C6 aliphatic dibasic esters and n-methyl-2 pyrolidone.

Examples of C8-C14 alcohol ester blends include EXXATE 900, 1000, 1200 from Exxon Chemical; glycols include propylene glycol, dipropylene glycol, and triproplylene glycol; and glycol ethers include dipropylene glycol monomethyl ether, propylene glycol monomethyl ether, propylene glycol-n-butyl ether, ethylene glycol monobutyl ether, and diethylene glycol monobutyl ether. Acid esters include methyl oleate and methyl linoleate, and diacid esters include methyl or butyl diesters of glutaric, adipic, and succinic acids. Petroleum hydrocarbons include AROMATIC 100, AROMATIC 150 ISOPAR M, and ISOPAR K.

Amines such as morpholine; 1,3-dimethyl-2-imidazolidinone; 1,3-propanediamine; 2-amino-1,3-propanediol; and 3-amino propanol; as well as alkanolamines such as triethanolamine, diethanolamine, 2-aminomethyl propanol, and monoethanolamine act as dispersants for contaminants and solubilize fatty acids and oils. Amino acids, provide nontoxic alternatives to monoethanolamine, and act as metal chelators. Methyl or isobutylesters of C4-C6 aliphatic dibasic esters and n-methyl-2 pyrolidone are also useful.

Other additives typically used in cleaning compositions may be used, including water softening agents, sequesterants, corrosion inhibitors, and antioxidants, which are added in amounts effective to perform their intended function. These additives and amounts thereof are well within the skill of the art.

Suitable water softening agents include linear phosphates, styrene-maleic acid co-polymers, and polyacrylates. Suitable sequesterants include 1,3-dimethyl-2-immidazolidinone; 1-phenyl-3-isoheptyl-1,3-propanedione; and 2 hydroxy-5-nonylacetophenoneoxime. Examples of corrosion inhibitors include 2-aminomethyl propanol, diethylethanolamine benzotraizole, and methyl benzotriazole. Antioxidants include, for example, (BHT) 2,6-di-tert-butyl-paracresol, (BHA) 2,6-di-tert-butyl-para-anisole, Eastman inhibitor O A BM-oxalyl bis (benzylidenehydrazide), and Eastman DTBMA 2,5-di-tert-butylhydroquinone.

In some embodiments, diluents can be added to the composition to aid sludge removal and, for example, reducing the viscosity of oil produced from the subject methods. Diluents can include, for example, naphthas, gas condensates, light crude oil, synthetic crude oil, gasoline, kerosene, MTBE, TAME, DME, alcohols (e.g., ethyl alcohol), ethane, propane, heptane, toluene and butanone, All additives should have a flash point greater than 100° F., preferably greater than 150° F. and more preferably 195° F. TCC to achieve a final product flash point greater than 200° F.

Use of Sludge Removal Compositions

In preferred embodiments, the subject invention provides a method for improving oil production efficiency by applying to a storage container having sludge therein, a composition comprising one or more microorganisms, one or more biosurfactants, one or more solvents and one or more ammonium salts.

The composition preferably comprises ingredients in amounts effective to reduce the interfacial tension of water and oil, thus releasing trapped impurities contained in crude oil and other fluids, and allowing the various phases therein to separate from one another.

The composition can be prepared and mixed prior to being applied to the storage container, or the individual components of the composition can be added separately to the storage container and mixed therein. In preferred embodiments, the storage container is an oil storage tank.

As used herein, "applying" a composition or product refers to contacting it with a target or site such that the composition or product can have an effect on that target or site. The effect can be due to, for example, microbial growth and/or the action of a microbial growth by-product. In certain embodiments, applying comprises pouring, spraying, brushing, soaking, coating or any other means of contacting the composition with a site (e.g., inner surface or space of a tank).

There are many types of contaminants associated with oil processing equipment, such as oils, waters, paraffins, asphalts/asphaltenes, resins, sulfur, tar by-products, and other viscous materials. The methods of the present invention can be used to remove any one or more of the contaminants associated with oil recovery, transmission and processing. In preferred embodiments, however, the contaminant is sludge or a component of sludge.

The composition of the subject invention may be applied directly to equipment for removal of sludge. The cleaning composition can be poured or injected into storage tanks and/or other types and varieties of equipment associated with gas and oil recovery, transmission, transportation and processing where water-in-oil emulsions might occur, and particularly, where rag layer and/or sludge accumulates. This includes, for example, gas and oil well casings, pumps, rods, pipes, lines, separators, and the like. In preferred embodiments, the cleaning compositions are applied to oil storage tanks, and/or refining separators having sludge therein.

In some embodiments, the composition may also be applied to crude oil, for example, prior to placing crude oil into a storage tank or separator tank. The composition can be poured into the tank, or the inner surfaces of the tank can be sprayed or coated with the composition, to aid in the prevention of sludge formation.

In one embodiment, the composition is a sludge cleaning composition of the subject invention. Optionally, the method can further comprise adding nutrients that are beneficial to microbial growth, such as, for example, sources of nitrogen, potassium, phosphorus, magnesium, proteins and/or carbon.

In one embodiment, the sludge cleaning composition is mixed within a storage container for a period of time sufficient to dissolve the sludge and form an emulsion comprising the composition and oil, water and sludge components. Mixing can be performed using any mixing device or technique, for example, a pump system that continuously circulates fluids out of and back into the tank, or an pump that injects fluids (e.g., gases (air) and/or liquids) under pressure and at a high velocity to continuously agitate and/or roil the contents of the tank. In one embodiment, the storage container has a built-in mixing system, for example, a mechanical stirring apparatus comprising rotating impellers or similar structures capable of circulating the contents of the tank throughout the entire volume of the tank.

Preferably, the mixing takes place continuously for a duration of about 1 to 6 hours or more, or at least 1, 2, 3, 4, 5 or 6 hours. Then, the emulsion can be allowed to sit for 2 to 3 hours, up to 12 to 24 hours, or until three separate layers form out of the emulsion: a top oil layer, a middle water and/or brine layer, and a bottom solid layer comprising, for example, sand, scale, clay, paraffins, asphaltenes and/or other solid sludge particles. In one embodiment, the top oil layer can comprise some heavy hydrocarbons, such as asphaltenes and paraffins. In one embodiment, the water layer can comprise yeast cells and/or yeast cell components.

In one exemplary embodiment, a method of removing rag, sludge, and/or other impurities from crude oil, includes the steps of pouring or injecting the composition into a storage tank with crude oil therein, and allowing it to mix with the crude fluid. The tank contents can then be circulated by, for example, a pump, for 24-72 hours, or 48-72 hours. Prior to circulating, the composition may be allowed to set for 8 to 24 hours, for example. The setting time, circulating time and dosage depend on, for example, the amount of crude in the tank, the amount of rag, sludge, and/or other impurities present, as well as the volume of the tank.

In some embodiments, the amount of the sludge cleaning composition added to a container can be determined based on, for example, a ratio of composition volume to sludge. In certain embodiments, the ratio of composition to sludge is about 10:1 to 2:1, about 9:1 to 3:1, about 8:1 to 4:1, about 7:1 to 5:1, or about 6:1. In specific embodiments, the composition to sludge ratio is about 2:1.

In one exemplary embodiment, a basic initial dosage can be, but is not limited to, 2 gallons of composition for every 1 gallons of sludge, and for maintenance, a dosage of, for example, about 20-25%, or less, of the initial dose on a periodic basis, e.g. weekly, biweekly, monthly, bimonthly, etc.

In one embodiment, the storage container is a large storage tank, for example, having a diameter of 300 to 400 feet. In certain embodiments, a portion of sludge can be removed from the large storage tank via robotic or manual methods and placed into a smaller storage tank, for example, a tank ⅓ or ½ the size of the large storage tank. Then, the methods according to the subject invention can be carried out in the smaller storage tank, which can reduce the time required for sludge remediation.

In one embodiment, the method further comprises, after the layers have separated within the tank, removing the top oil layer from the storage tank and placing the oil layer into a centrifuge. Advantageously, in one embodiment, the oil layer has less sand and scale remaining in it than it would have if it were not treated with the subject composition. Thus, the centrifuge can operate at a faster speed, thereby reducing the amount of time required for the centrifuge process to separate the layers. Accordingly, residual oil can be separated in a matter of hours or days to be sent to oil refineries. Furthermore, the residual oil that is recovered from the centrifuge can be processed and/or refined more efficiently than untreated residual oil.

In one embodiment, after the oil layer is removed from the storage tank, the water and/or brine phase layer can be removed, for example, by pumping. The water and/or brine can be sent to a water treatment facility, and/or it can be recycled, for example, as frac fluid in fracking wells.

After the oil and water layers have been removed from the storage tank, the solid sludge sediment layer is left behind. In one embodiment, the storage tank and sludge therein can be treated again with the sludge cleaning composition. For example, the sludge cleaning composition can be applied to the tank, mixed, and then allowed to sit and dissolve and/or separate the remaining sludge. This can be repeated as many times as necessary.

In one embodiment, the remaining sludge layer can be manually or mechanically removed from the tank, using robotics, mechanized excavation techniques, or using shovels and manpower. Whether to apply the sludge cleaning composition or to manually remove the remaining sludge can depend upon, for example, the thickness of the remaining layer, the composition and/or age of the sludge, the size of the tank, and other factors.

The subject compositions and methods can be administered in sludge-containing tanks utilized during production, transportation, storage, and/or refining of crude oil. For example, the subject products can be applied to a storage tank at or near the site of recovery, a tanker used for transporting the oil, and/or a tank where crude oil is deposited and held prior to refining.

In one embodiment, methods are provided for treating, for example, a borehole, oilfield, and/or oil and gas transportation, transmission and/or refinery equipment. In certain embodiments, the methods are used to improve oil production, as well as maintenance of, for example, pipes, drills and other structures and equipment involved in oil and/or gas production, transportation, storage and/or refining.

In some embodiments, the cleaning composition may be applied with a substance that promotes adherence of the microbe-based product to a surface to be treated. The adherence-promoting substance may be a component of the composition or it may be applied simultaneously with, or sequentially with, the composition. Adherence-promoters can include organic or inorganic particles, ions such as calcium, magnesium, phosphate, and sodium, iron, carbon sources that are metabolized to acetyl coenzyme A, acetyl phosphate, and acetate.

Up to, for example, 50 wt. % or more of additives may also be applied, as needed, for particular applications, such as to vary the VOC levels, increase penetration of the mixture, decrease viscosity of the mixture, as couplers for solvent insolubles in the mixture, and for other purposes determined by a skilled artisan having the benefit of the subject disclosure.

Production of Microorganisms

The subject invention provides methods for cultivation of microorganisms and production of microbial metabolites and/or other by-products of microbial growth. In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

In certain embodiments, a microbe growth facility produces fresh, high-density microorganisms and/or microbial growth by-products of interest on a desired scale. The microbe growth facility may be located at or near the site of application, or at a different location. The facility produces high-density microbe-based compositions in batch, quasi-continuous, or continuous cultivation.

In certain embodiments, the microbe growth facilities of the subject invention can be located at or near the location where the microbe-based product will be used (e.g., at or near an oil well) For example, the microbe growth facility may be less than 300, 250, 200, 150, 100, 75, 50, 25, 15, 10, 5, 3, or 1 mile from the location of use.

The microbe growth facilities can produce fresh, microbe-based compositions, comprising the microbes themselves, microbial metabolites, and/or other components of the medium in which the microbes are grown. If desired, the compositions can have a high density of vegetative cells or a mixture of vegetative cells, spores, conidia, mycelia and/or other microbial propagules. Advantageously, the compositions can be tailored for use at a specified location. In one embodiment, the microbe growth facility is located on, or near, a site where the microbe-based products will be used.

Advantageously, in preferred embodiments, the methods of the subject invention harness the power of naturally-occurring local microorganisms and their metabolic by-products to improve oil production, transmission and/or refining. Local microbes can be identified based on, for example, salt tolerance, ability to grow at high temperatures, and the use of genetic identification of the sequences described herein.

The microbe growth facilities provide manufacturing versatility by their ability to tailor the microbe-based products to improve synergies with destination geographies. The microbe growth facilities may operate off the grid by utilizing, for example, solar, wind and/or hydroelectric power. Thus, the microbe-based compositions can be produced in remote locations.

The growth vessel used for growing microorganisms can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the cultivation utilizes a medium supplemented with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

In one embodiment, the cultivation supplies oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of the liquid, and air spargers for supplying bubbles of gas to the liquid for dissolution of oxygen into the liquid.

In one embodiment, the cultivation utilizes a medium supplemented with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, isopropyl, propanol, butanol, pentanol, hexanol, isobutanol, and/or glycerol; fats and oils such as soybean oil, rice bran oil, canola oil, olive oil, corn oil, sesame oil, and/or linseed oil; etc. These carbon sources may be used independently or in a combination of two or more.

In one embodiment, the method comprises use of two carbon sources, one of which is a saturated oil selected from canola, vegetable, corn, coconut, olive, or any other oil suitable for use in, for example, cooking. In a specific embodiment, the saturated oil is 15% canola oil or discarded oil that has been used for cooking.

In one embodiment, the microorganisms can be grown on a solid or semi-solid substrate, such as, for example, corn, wheat, soybean, chickpeas, beans, oatmeal, pasta, rice, and/or flours or meals of any of these or other similar substances.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, sodium chloride and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

In one embodiment, the method for cultivation of microorganisms is carried out at about 5° to about 100° C., preferably, 15 to 60° C., more preferably, 25 to 50° C. In a further embodiment, the cultivation may be carried out continuously at a constant temperature. In another embodiment, the cultivation may be-subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention provides methods of producing a microbial metabolite by cultivating a microbe strain of the subject invention under conditions appropriate for growth and production of the metabolite; and, optionally, purifying the metabolite. In a specific embodiment, the metabolite is a biosurfactant. The metabolite may also be, for example, solvents, acids, ethanol, lactic acid, manno-proteins, beta-glucan, proteins, amino acids, peptides, metabolic intermediates, polyunsaturated fatty acids, and lipids. The metabolite content produced by the method can be, for example, at least 20%, 30%, 40%, 50%, 60%, 70%, 80%, or 90%.

The biomass content of the fermentation medium may be, for example from 5 g/l to 180 g/l or more, or from 10 g/l to 150 g/l.

The microbial growth by-product produced by microorganisms of interest may be retained in the microorganisms or secreted into the growth medium. In another embodiment, the method for producing microbial growth by-product may further comprise steps of concentrating and purifying the microbial growth by-product of interest. In a further embodiment, the medium may contain compounds that stabilize the activity of microbial growth by-product.

The method for cultivation of microorganisms and production of the microbial by-products can be performed in a batch, quasi-continuous, or continuous processes.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a microbe-free medium or contain cells, spores, mycelia, conidia or other microbial propagules. In this manner, a quasi-continuous system is created.

Advantageously, the methods of cultivation do not require complicated equipment or high energy consumption. The microorganisms of interest can be cultivated at small or large scale on site and utilized, even being still-mixed with their media. Similarly, the microbial metabolites can also be produced at large quantities at the site of need.

Because, in certain embodiments, the microbe-based products can be generated locally, without resort to the microorganism stabilization, preservation, storage and transportation processes of conventional microbial production, a much higher density of live microbes, spores, mycelia, conidia or other microbial propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, smaller supplies of starter material, nutrients and pH control agents), which makes the system efficient. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have undergone vegetative cell stabilization, have been sporulated or have sat in the supply chain for some time. The microbe-based products of the subject invention are particularly advantageous compared to traditional products wherein cells, spores, mycelia, conidia and/or other microbial propagules have been separated from metabolites and nutrients present in the fermentation growth media. Reduced transportation times allow for the production and delivery of fresh batches of microbes and/or their metabolites at the time and volume as required by local demand.

Advantageously, local microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell- and/or propagule-count product and the associated growth medium and metabolites in which the microbes are originally grown.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

Preparation of Microbe-Based Products

One microbe-based product of the subject invention is simply the fermentation medium containing the microorganism and/or the microbial metabolites produced by the microorganism and/or any residual nutrients. The product of fermentation may be used directly without extraction or purification. If desired, extraction and purification can be easily achieved using standard extraction and/or purification methods or techniques described in the literature.

In one embodiment, a first yeast fermentation product can be obtained via cultivation of a yeast, e.g., *Wickerhamomyces anomalus*, using a modified form of solid state fermentation. The culture can be grown on a substrate with ample surface area onto which the yeasts can attach and propagate, such as, for example, rice, soybeans, chickpeas, pasta, oatmeal or beans. The entire fermentation medium with yeast cells growing throughout, and any growth by-products thereof (e.g., enzymes, solvents, and/or biosurfactants), can be harvested after, for example, 3-5 days of cultivation at 25-30° C. The culture can be blended with the substrate, milled and/or micronized, and optionally, dried.

In an alternative embodiment, the first yeast fermentation product is obtained using submerged fermentation, wherein the yeast fermentation product comprises liquid broth comprising cells and any yeast growth by-products. A liquid medium containing necessary sources of carbon, nitrogen, minerals and optionally, antimicrobial substances to prevent contaminating bacterial growth can be used. The culture can be grown with an additional carbon source, particularly, a saturated oil (e.g., 15% canola oil, or used cooking vegetable oil). Typically, the pH begins at 5.0-5.5, then decreases to 3.0-3.5, where it is stabilized. The fermentation broth with cells and yeast growth by-products, which can be harvested after, for example, 24-72 hours of cultivation at 25-30 °C., comprises this alternative form of the Star 3+ product.

The composition, which can comprise, $1 \times 10^6$ to $1 \times 10^{12}$ cells/gram, can be mixed with water, brine fluids and/or oil, and if desired, diluted, for example, up to 10, 50, 100, 500, or 1,000 times prior to use.

The microorganisms in the microbe-based product may be in an active or inactive form. In one embodiment, the microbes are active. The microbe-based products may be used without further stabilization, preservation, and storage. Advantageously, direct usage of these microbe-based products preserves a high viability of the microorganisms up until inactivation, reduces the possibility of contamination from foreign agents and undesirable microorganisms, and maintains the activity of the by-products of microbial growth.

The microbes and/or medium (e.g., broth or solid substrate) resulting from the microbial growth can be removed from the growth vessel and transferred via, for example, piping for immediate use.

In one embodiment, the microbe-based product is simply the growth by-products of the microorganism. For example, biosurfactants produced by a microorganism can be collected from a submerged fermentation vessel in crude form, comprising, for example about 0.001% to about 99% pure biosurfactant in liquid broth.

In other embodiments, the microbe-based product (microbes, medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 gallon to 1,000 gallons or more. In other embodiments the containers are 2 gallons, 5 gallons, 25 gallons, or larger.

Upon harvesting, for example, the yeast fermentation product, from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, solvents, biocides, other microbes and other ingredients specific for an intended use.

Other suitable additives, which may be contained in the formulations according to the invention, include substances that are customarily used for such preparations. Examples of such additives include surfactants, emulsifying agents, lubricants, buffering agents, solubility controlling agents, pH adjusting agents, preservatives, stabilizers and ultra-violet light resistant agents.

In one embodiment, the product may further comprise buffering agents including organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt such as sodium bicarbonate or carbonate, sodium sulfate, sodium phosphate, sodium biphosphate, can be included in the formulation.

Advantageously, in accordance with the subject invention, the microbe-based product may comprise medium in which the microbes were grown. The product may be, for example, at least, by weight, 1%, 5%, 10%, 25%, 50%, 75%, or 100% growth medium. The amount of biomass in the product, by weight, may be, for example, anywhere from 0% to 100%, 10% to 90%, 20% to 80%, or 30% to 70%, inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures.

We claim:

1. A method for cleaning sludge from an oil storage tank, the method comprising:
    applying a cleaning composition comprising one or more microorganisms, one or more biosurfactants, and one or more solvents to a storage tank having sludge therein;
    mixing the composition with the sludge to form an emulsion; and
    allowing the emulsion to sit for 3 to 24 hours, until three separate phase layers form in the tank, wherein the three phase layers are a top oil layer, a middle water layer and a bottom solids layer, wherein the one or more microorganisms comprise inactive *Starmerella bombicola* and/or *Wickerhamomyces anomalus*, wherein the one or more biosurfactants comprise sophorolipids and/or rhamnolipids, and wherein the one or more solvents comprise ethanol, methanol and/or isopropyl alcohol.

2. The method of claim 1, wherein the composition is applied to the storage tank in an amount that is from 2 times to 10 times the amount of sludge in the tank.

3. The method of claim 1, wherein mixing is achieved using a pump to inject a gas or liquid into the tank under pressure and/or using a mechanical stirring apparatus comprising a rotating impeller.

4. The method of claim 1, wherein mixing occurs for a duration of about 1 to 6 hours.

5. The method of claim 1, used to improve oil production, wherein the method further comprises removing the top oil layer from the storage tank; centrifuging the oil layer to separate out residual oil from solids remaining in the oil layer; and sending the residual oil to a refinery to be refined.

6. The method of claim 5, which further comprises pumping the middle water layer from the storage tank, leaving behind the bottom solids layer in the tank, and sending the water to a treatment facility.

7. The method of claim 6, which further comprises removing the bottom solids layer from the storage tank using mechanical or manual techniques.

\* \* \* \* \*